US008439916B2

(12) United States Patent
Coati et al.

(10) Patent No.: US 8,439,916 B2
(45) Date of Patent: May 14, 2013

(54) INTRAMEDULLARY NAIL WITH SHAPE MEMORY ELEMENTS

(75) Inventors: Michele Coati, San Pietro in Caricano (IT); Mara Bagnasco, Milan (IT); Luigi Rossi, Peschiera del Garda (IT); Graziano Marini, Castel D'Azzano (IT); Graziano Rossi, Verona (IT)

(73) Assignee: Orthofix S.r.l. (IT)

( * ) Notice: Subject to any disclaimer, the term of this patent is extended or adjusted under 35 U.S.C. 154(b) by 232 days.

(21) Appl. No.: 13/030,985

(22) Filed: Feb. 18, 2011

(65) Prior Publication Data

US 2012/0172876 A1 Jul. 5, 2012

(30) Foreign Application Priority Data

Dec. 31, 2010 (EP) ...................................... 10197452

(51) Int. Cl.
*A61B 17/72* (2006.01)
(52) U.S. Cl.
USPC ........................................................... 606/62
(58) Field of Classification Search ............. 606/62–68, 606/304, 313, 323, 326, 327
See application file for complete search history.

(56) References Cited

U.S. PATENT DOCUMENTS

| 6,120,504 | A | 9/2000 | Brumback et al. |
| 2005/0159749 | A1* | 7/2005 | Levy et al. ...................... 606/72 |
| 2008/0262495 | A1 | 10/2008 | Coati et al. |

FOREIGN PATENT DOCUMENTS

| DE | 202005020788 U1 | 7/2006 |
| EP | 2133034 A1 | 12/2009 |

* cited by examiner

*Primary Examiner* — Eduardo C Robert
*Assistant Examiner* — David Comstock
(74) *Attorney, Agent, or Firm* — Akerman Senterfitt

(57) ABSTRACT

An intramedullary nail for a fractured elongated bone, comprising a cannulated rod having proximal and distal ends; an outside tubular sleeve for coaxially hosting and guiding the rod; and shape memory elements hosted in corresponding seats of the rod. Each shape memory element can be retractably housed in its respective seat in a first configuration, allowing insertion of the nail into the bone, and can project from a sleeve opening in another configuration. Proximal and distal pairs of the elements are provided at the proximal and distal rod ends. The proximal element pair lie on a same plane and are kept in their seats by a proximal cover. The distal element pair lie on an offset plane to the plane of the proximal element pair and are kept in their seats by a distal cover. This removes the need for bone screws to stabilize the nail inside the medullary canal.

12 Claims, 8 Drawing Sheets

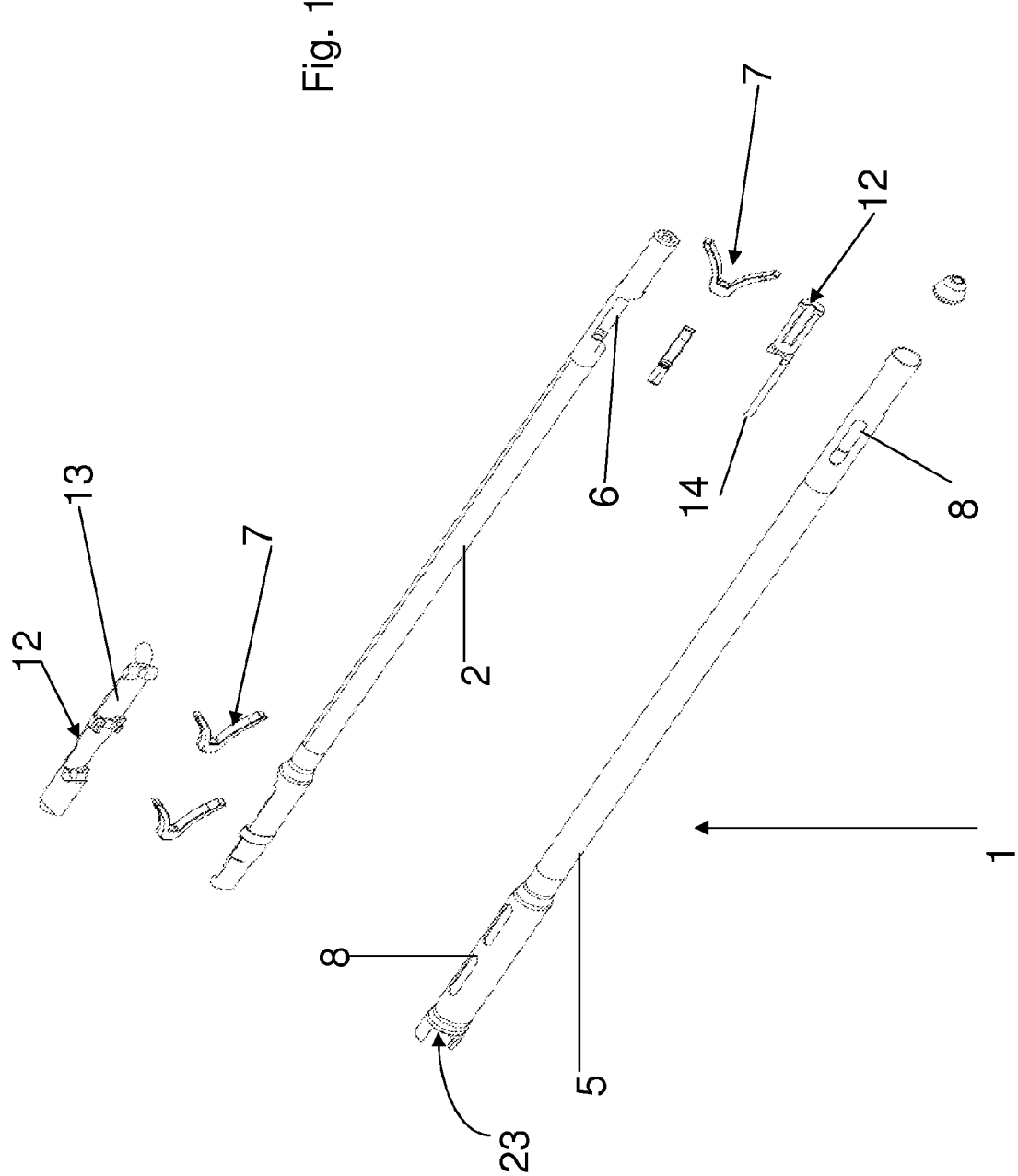

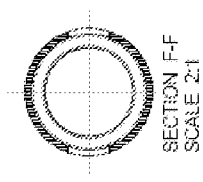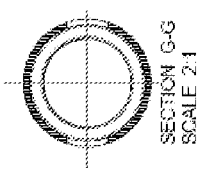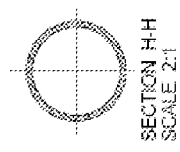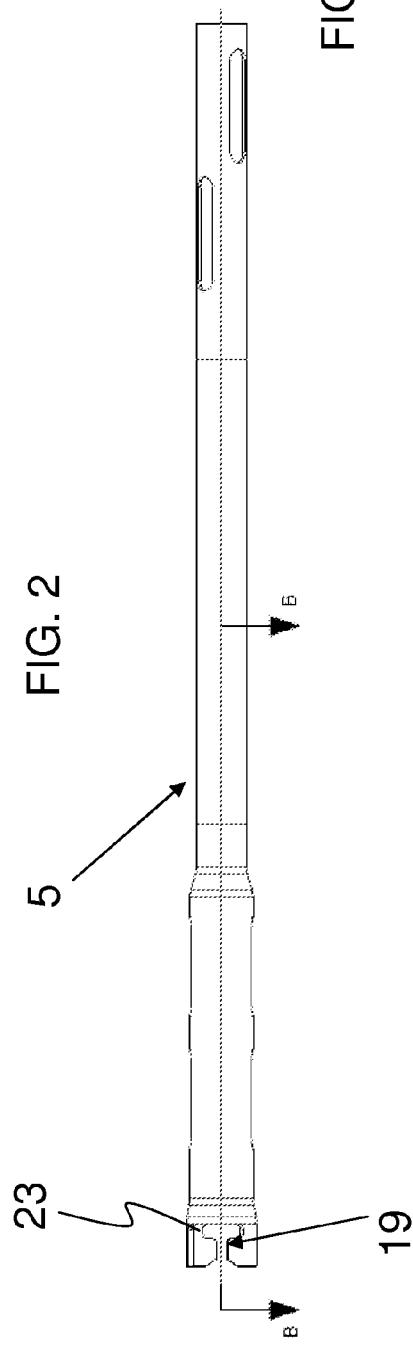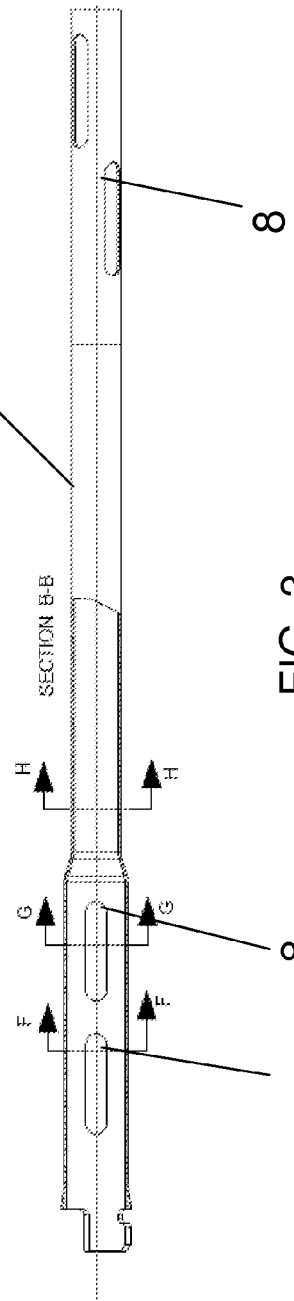

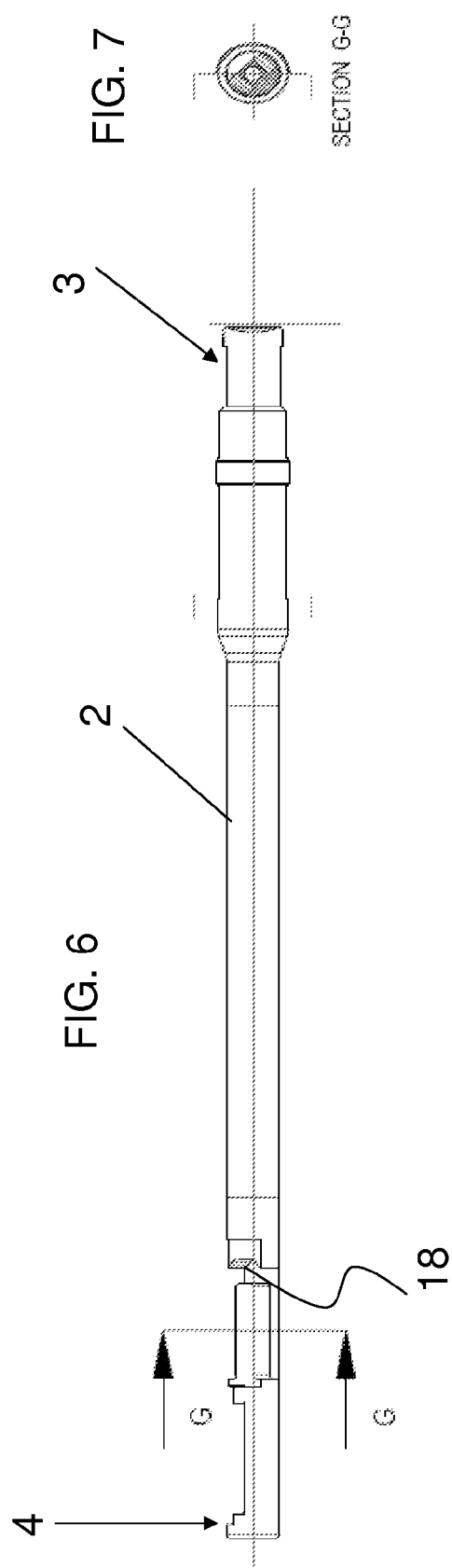
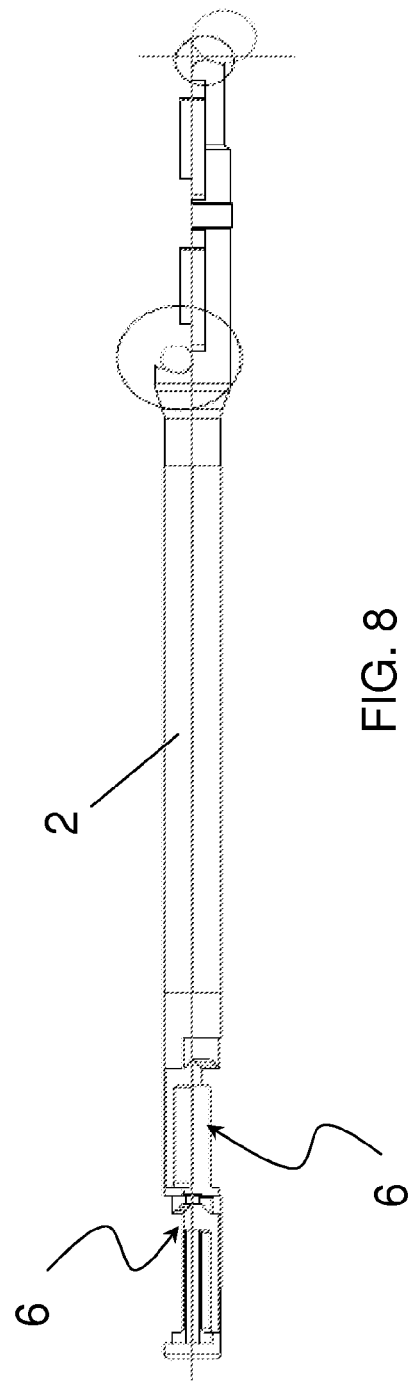

INTRAMEDULLARY NAIL WITH SHAPE MEMORY ELEMENTS

CROSS-REFERENCE TO RELATED APPLICATIONS

The present application claims priority to European Patent Application No. 10197452.5, filed Dec. 31, 2010, the entirety of which is incorporated herein by reference.

FIELD OF APPLICATION

The present invention refers, in its most general aspect, to an Intramedullary nail suitable to be inserted into a fractured elongated bone, for example a femur or a tibia, and comprising a cannulated rod extending between a proximal end and a distal end.

More particularly, the invention relates to a nail comprising:
- a cannulated rod extending between a proximal end and a distal end;
- an outside tubular sleeve for hosting said rod, the rod being coaxial with the sleeve and axially or angularly guided inside the tubular sleeve;
- shape memory elements hosted in corresponding seats of said rod; each elements being able to assume a configuration wherein is retractably housed in its respective seats, so to allow the insertion of the nail in the bone, and another configuration wherein said elements are projecting from slots opening of said sleeve.

PRIOR ART

Intramedullary nails are known in the art to be used in surgical interventions and to be inserted into a fractured elongated bone to return consistency to the bone so that the bone callus regeneration mechanism can take place correctly Those nails comprise a stem or rod having a cylindrical shape either solid or hollow, in this last case the rod is cannulated.

In order to fix the intramedullary nail to the bone portions to be reconstructed, two offset holes are usually provided on the nail, having axes lying on parallel planes and extending diametrically across the rod in correspondence with the nail distal end. Other two offset holes are generally provided in correspondence with the nail proximal end with axes lying on parallel planes.

All these holes are suitable for housing bone screws that inserted in the bone after a convenient bone drilling thus fixing the intramedullary nail inside the fractured bone.

Although still widely used those known nails have known drawbacks due to bone drillings performed for the bone screw insertion in correspondence with the holes of the inserted intramedullary nail. Since the nail holes are no visible, X rays technique is involved with cumulative exposure of the operating staff and being quite awkward during the surgical operation.

Alternative nail structures have been provided in more recent times. For instance the European patent No. EP 1 740 113 owned by the same Applicant discloses an Intramedullary nail suitable for insertion in a fractured elongate bone and comprising a straight stem extending between a proximal end and a distal end and further comprises a plurality of elements realised with at least a shape-memory material. A free end of said shape-memory elements being positioned outwards the stem for the nail fixation to the bone.

Whilst advantageous from many points of views, such nails with shape-memory elements have some drawbacks that are still to be overcome. For instance, the total missing of bone screws does not ensure complete stabilisation of the nail inside the medullary canal and against a high axial stress determined by the weight of a patient's body. If such stress is applied the nail becomes unstable and might even compromise the process of osteosynthesis as well as causing anomalies in the healing process.

A further prior art solution is disclosed in the other European application No. EP 2 133 034 owned by the same applicant. This further prior art discloses an Intramedullary nail to be inserted into a fractured long bone comprising a cannulated rod coaxially inserted into a tubular sleeve; a transversal hole is formed at the proximal end of the rod and the sleeve to host a stop screw holding the nail in a stable position within the medullay canal.

This solution simplifies the nail structure of the nails comprising only shape-memory material but it is still a compromise that require surgery for inserting the stop screw for stabilizing the nail inside the bone.

The technical problem of the present invention is that of providing a Intramedullary nail having such structural and functional features to overcome all the drawbacks of the prior art solutions by a simpler nail construction for hosting the shape memory elements.

Another object of the nail of the present invention is that of providing a nail that do not require bone screws to be stabilized inside the medullary canal.

A further object of the present invention is that of avoiding any danger of bone dysmetria and rotation of the limb during the period of nail hosting inside the bone.

SUMMARY OF THE INVENTION

The solution idea at the basis of the present invention is that of providing a nail including an internal rod and an external sleeve and comprising shape memory elements associated to said rod; the rod having a very simple construction including seats for the memory elements just in the proximal and distal portions and keeping the shape elements in their seats by corresponding covers that are part of the rod. This allows realizing with only few components nails having shape memory elements laying on different planes without using bone screws for stabilizing the nail inside the medullary canal.

Based upon this idea for a solution, the technical problem is solved according to the invention by an Intramedullary nail to be inserted into a fractured elongated bone and comprising:
- a cannulated rod extending between a proximal end and a distal end;
- an outside tubular sleeve for hosting said rod, the rod being coaxial with the sleeve and axially or angularly guided inside the tubular sleeve;
- shape memory elements hosted in corresponding seats of said rod; each elements being able to assume a configuration wherein is retractably housed in its respective seats, so to allow the insertion of the nail in the bone, and another configuration wherein said elements are projecting from slots opening of said sleeve;

characterized in that:
- a proximal couple of said shape memory elements is provided at the rod proximal end and a distal couple of said elements is provided at the rod distal end;
- the shape memory elements of the proximal couple laying on a same plane and being kept in their corresponding seats by a proximal cover;

the shape memory elements of the distal couple laying on a offset plane with respect to the laying plane of the elements of the proximal couple and being kept in their corresponding seats by a distal cover.

Advantageously, the first and second shape memory element of the distal couple are 90° angularly spaced one from the other.

More particularly, a shape memory element of the distal couple is located on a plane at 45° with respect to the laying plane of the elements of the proximal couple while the other element of the distal couple is located on a plane at −45° with respect to the laying plane of the elements of the proximal couple.

It should be noted that the shape memory elements are realized by SIM (Stress Induced Martensite) materials, for instance Nitinol.

Moreover, the distal cover is formed by two portions that are connected by one corner and are extended in perpendicular planes. Both said portions have an outside concave surface that reproduces the continuity of the cylindrical rod when the distal cover is mounted and fixed to the rod to keep in position the distal couple of shape memory elements.

The proximal cover is formed by an elongated portion integrally formed with a tubular top portion including an internal thread corresponding to the thread internally formed at the proximal end of the rod.

Further features and advantages of the Intramedullary nail according to the invention shall become clearer from the following description of an example embodiment thereof, given for indicating and not limiting purposes with reference to the attached drawings.

BRIEF DESCRIPTION OF THE DRAWINGS

FIG. 1 illustrates a perspective view of a nail according to the invention split in its component portions;

FIG. 2 illustrates a side view of a particular of the nail of FIG. 1;

FIG. 3 illustrate a longitudinal cross section of the particular of FIG. 2 taken along the line B-B;

FIGS. 4A-4C illustrate different views of transversal cross sections a of the particular of FIG. 2 taken along the lines F-F; G-G and H-H;

FIG. 6 illustrates a side view of a particular of the nail of FIG. 1;

FIG. 7 illustrate a longitudinal cross section of the particular of FIG. 6 taken along the line G-G;

FIG. 8 illustrates a side view of the particular of FIG. 6 rotated by 90°;

DETAILED DESCRIPTION

Figure 5D:
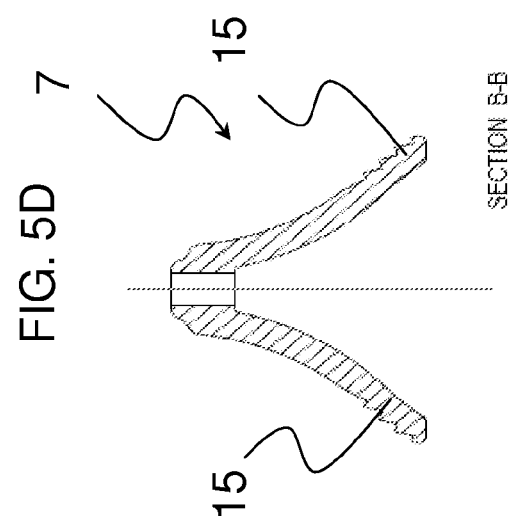
FIGS. 5A-5D illustrate front, side, top and cross section view of a shape memory element incorporated in the nail of the present invention.
Figure 5B:
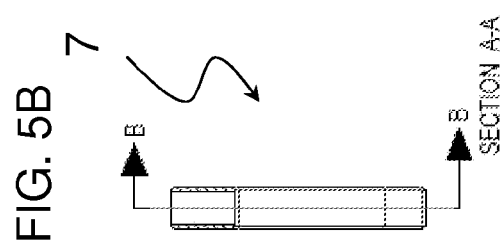
Figure 5A:
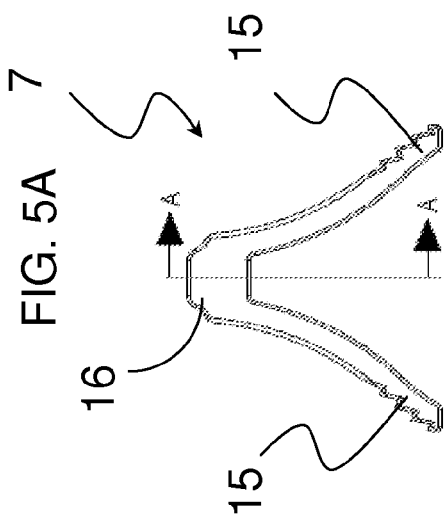
Figure 5C:
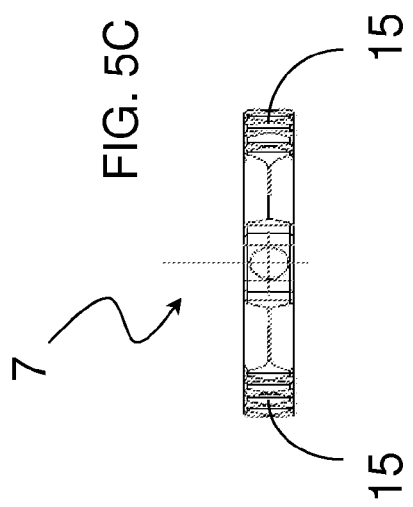
Figure 10:
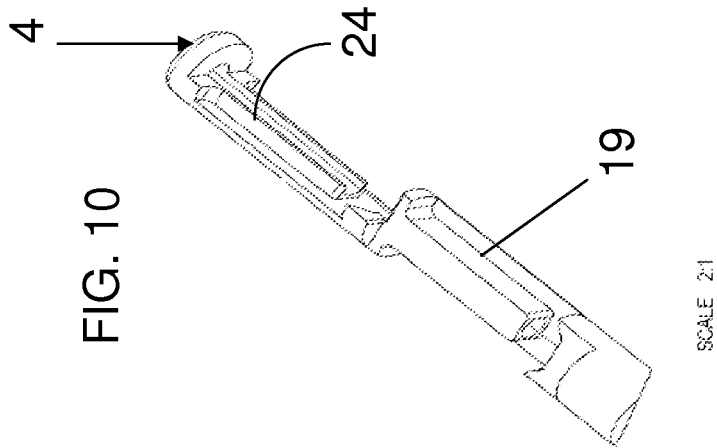
FIG. 10 illustrates a perspective view of the distal end of FIG. 9 in a reversed position.
Figure 9:
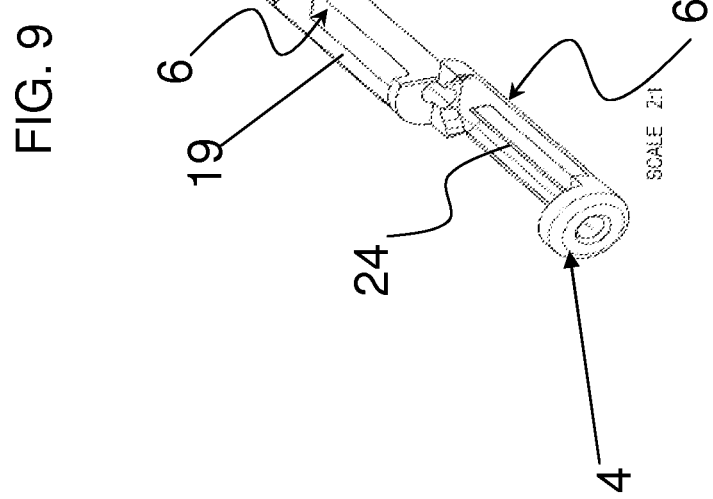
FIG. 9 illustrates a perspective view of a detail of the distal end of the particular of FIG. 6 with seats for the shape memory elements of FIGS. 5A-5D.
Figure 11:
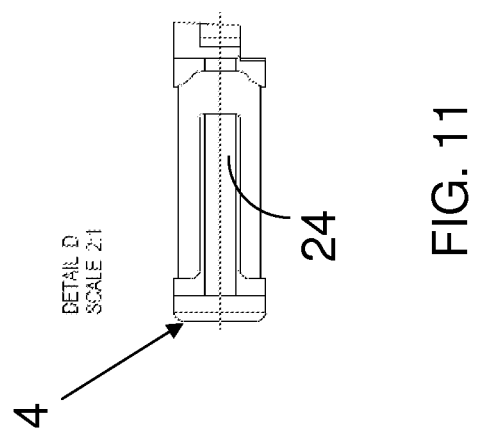
FIG. 11 is a top view of the same distal end of FIGS. 9 and 10.
Figure 12:
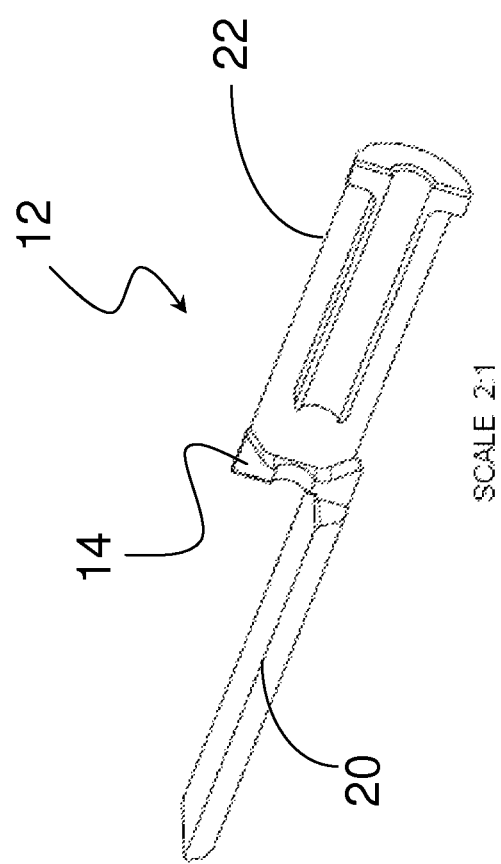
FIG. 12 is a perspective view of another particular of the nail of FIG. 1, a distal cover portion of the internal rod.
Figure 13:
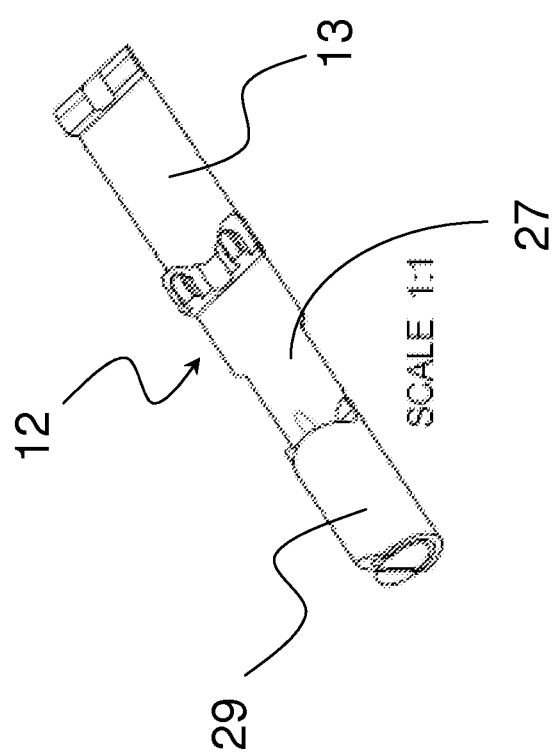
FIG. 13 is a perspective view of another particular of the nail of FIG. 1, a proximal cover portion of the internal rod.
Figure 14:
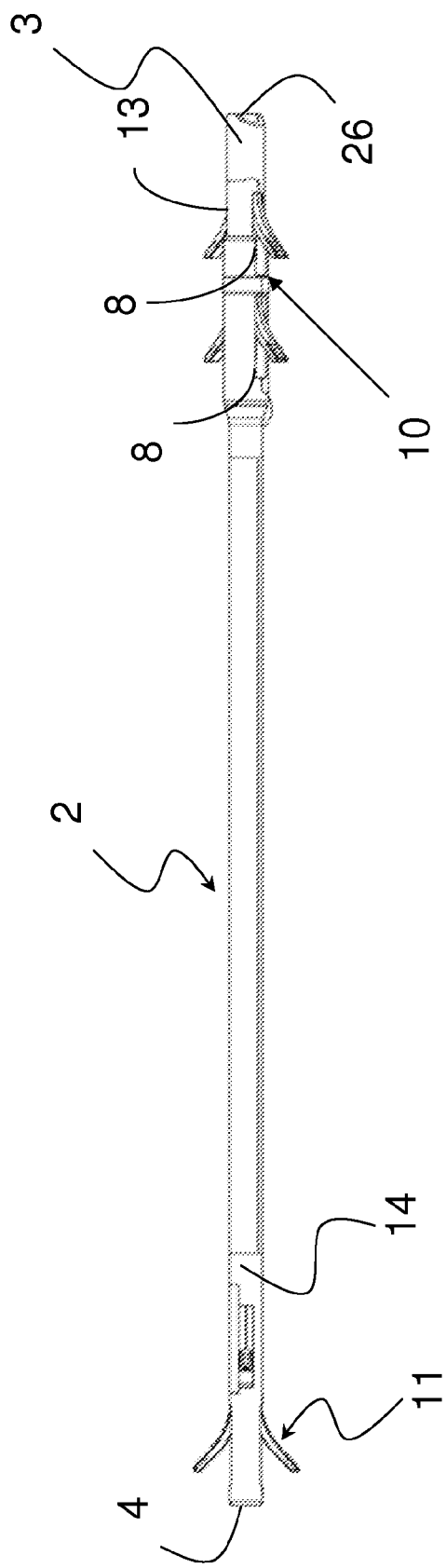
FIG. 14 is a top view of the nail of the present invention in its assembled configuration.

With reference to the aforementioned figures, 1 generally indicates an intramedullary nail in accordance with the present invention, intended to be inserted into a fractured long bone, for instance a femur.

In case of femoral nail, the nail 1 is provided with an anatomic shape having proximal bent of 5° to follow the shape of the femoral bone. So, the nail 1 and its main components are curved or bent so that the proximal end forms a small angle of 5° with the distal end.

The nail 1 comprises an inner rod 2 extending between a proximal end 3 and a distal end 4.

The nail 1 further comprises an outside tubular sleeve 5 hosting the rod 2 that is inserted coaxially into the tubular sleeve 5. Preferably, the nail 1 and its main components, the rod 2 and the sleeve 5 are cylindrical.

The rod 2 is cannulated, that is to say that it has an internal cavity extending for at least a portion along a longitudinal axis, indicated with X. The rod may be totally cannulated for all its length and this feature is used to host a guide wire, for example a Kirschner wire, for use during the insertion in the bone medullary canal.

In accordance with the present invention the inner rod 2 is sliding or swivelling hosted inside the tubular sleeve 5. More specifically, the rod 2 is axially movable inside the sleeve 5 and driven by an external device linked to the proximal end of the nail 1. However, even a relative rotation of the rod inside the sleeve could be realized according to the needs. What is important is that the relative axial or angular guided movement of the rod 2 inside the sleeve 5 could bring to a coincidence between slot openings 8 in the sleeve 5 and active elements 7 hosted along the rod.

In a head portion of the rod 2 a threading 26 is provided for a threaded connection with a suitable driving tool, not shown, for gripping the rod 2 of the nail 1.

In order to allow easy insertion of the nail 1 in the medullary canal it is foreseen an external instruments that may be connected to the proximal end of the tubular sleeve 5. For allowing this connection the proximal end is shaped with an attachment system 23, for instance of the bayonet type; however, any other fastening system known in the field can be used.

The rod 2 comprises some seats 6 for hosting corresponding active elements 7 realised with at least a shape-memory material. These seats are in the form of recesses 21 for hosting the central portion or core 16 of the active elements 7.

The active elements 7 are preferably similar to each other.

The element 7 have the form of little wings 15 connected by the central core 16 and because of their shape memory feature they can assume different configurations from a first configuration wherein they are totally hidden inside their seat 6 to an extended configuration wherein they are protruding through corresponding slot openings 8 provided in the sleeve 5.

In other words, the active elements 7 are structured and suitable to take a first shape or configuration, wherein each elements 7 is retractably housed in its respective seats 6, so to allow the insertion of the nail in the bone. Another shape or configuration is taken wherein said active elements 7 are projecting from the respective seats 6 for abutting and gripping the internal wall of the medullary canal of the fractured bone.

With the term "shape memory material" we mean a material, known in the art, having a given starting shape and taking, under predetermined external conditions or undergoing a predetermined activation condition, called also "material instruction", a given new shape but returning to the initial shape conditions when the material instructions are deactivated.

For the meaning of the present invention, the starting shape may correspond to the configuration wherein the shape-memory elements 7 are arranged projecting from the seats 6 of the rod 2. However, according to the material used, the starting shape might even correspond to the configuration wherein the elements 7 are retracted.

It must be noted that, while the shape memory elements 7 may be realized with SME such as a Shape Memory Alloy, it is preferable to use SIM materials, that is to say: materials sensible to Stress Induced Martensite, for instance Nitinol.

Another characteristic of the shape-memory material stays in that the transition from the first to the second shape, or configuration, is reversible, i.e. the shape-memory elements can be transformed from the second to the first shape, or configuration, allowing the extraction of the nail from the bone.

The nail 1 of the invention is structured with a couple 10 of elements 7 located at the proximal end 3 of the nail and laying on a same plane, thus having the wings extending in such a plane. We will call proximal couple this first couple 10 of elements 7.

Another couple 11 of elements 7 is provided at the distal end 4 of the nail 1. We will call distal couple this second couple 11 of elements 7.

Advantageously, the laying plane of one shape memory element 7 of the distal couple 11 is oriented at 45° with respect to the laying plane of the wings 15 of the shape memory elements 7 of the proximal couple 10.

The other element of the distal couple 11 is oriented at −45° with respect to the laying plane of the wings 15 of the shape memory elements 7 of the proximal couple 10.

Therefore, the first and second element 7 of the distal couple 11 are angularly spaced (or displaced) of 90° one from the other.

The fact that the distal elements 7 are offset with one another, for example with a offset of sexagesimal 90°, ensures a determined stability on orthogonal planes and it is useful for allowing a better gripping of the nail 1 inside the medullary canal.

Advantageously, the memory shape elements of the present invention are structurally independent from the rod 2 and are hosted in their corresponding seat 6 of the rod but firmly kept in such seat by a cover 12. The central core 16 of each elements 7 is firmly kept between the seat 6 and the cover 12, while the wings 15 of the elements 7 are movable through openings left between the cover 12 and the rod 2 and through the slot openings 8.

A proximal cover 13 is provided for the proximal couple 10 of shape memory elements 7 and a distal cover 14 is provided for the distal couple 11 of shape memory elements 7.

The proximal cover 13 and the distal cover 14 have respective shapes that are conjugated with the shape and relative position of the proximal couple 10 of shape memory elements 7 and the distal couple 11 of shape memory elements 7 to be covered.

Each cover 13 or 14 is fixed to the corresponding proximal or distal rod portion by soldering or other fixing techniques.

The covers 13 and 14, once fixed to the rod, might be considered integral with the rod so that each seat 6 is formed by a passing opening 18 for hosting the core 16 of a shape memory element 7 and by a couple of opposite recesses 19 for hosting each wing 15 of the same shape memory element 7 when in the retracted configuration.

In more detail, the distal cover 14 is formed by two portions 20 and 22 that are connected at one corner and are extended in perpendicular planes.

Both portions 20, 22 have an outside concave surface that reproduces the continuity of the cylindrical rod 2 when the distal cover is mounted and fixed to the rod 2 to keep in position the distal couple 11 of shape memory elements 7.

The first portion 20 of the distal cover 14 is internally flat while the other portion 22 is shaped in order to abut against a corresponding and conjugated internal portion 24 of the last distal seat 6.

The coupling between the distal cover 14 and the corresponding seats 6 always guarantee the continuity of the cannulated rod 2.

As to the proximal cover 13, it is formed by an elongated portion 27 integrally formed with a short tubular top portion 29 including an internal thread 26 corresponding to the thread internally formed at the proximal end of the rod 2.

The external surface of the elongated portion 27 for part of the outside concave surface of the proximal portion of the rod 2.

For facilitating the insertion of the nail 1 in the medully canal of the fractured bone, the tip portion of the rod 2 is preferably rounded so as to allow a sliding of the nail in said medullary canal.

As can be appreciated from what has been described, the intramedullary nail according to the present invention meets the requirements and overcomes the drawbacks mentioned in the introductory part of the present description with reference to the prior art.

A clear advantage of the nail according to the present invention is due to the fact that no screws are needed to stabilize the nail in the medullary canal.

Another advantage of the use of shape-memory elements in that they are structurally independent from the nail rod and this allows to realise a non shape-memory material rod with substantial reduction of the production cost.

Of course, a person skilled in the art can apply numerous modifications and variants to the intramedullary nail described above, in order to satisfy contingent and specific requirements, all of which are covered by the scope of protection of the invention, as defined by the following claims.

The invention claimed is:

1. An intramedullary nail to be inserted into a fractured elongated bone comprising:
a cannulated rod extending between a proximal end and a distal end;
an outside tubular sleeve for hosting said rod, the rod being coaxial with the sleeve and axially or angularly guided inside the tubular sleeve;
shape memory elements hosted in corresponding seats of said rod; each element being able to assume a first configuration wherein it is retractably housed in its respective seat, so to allow the insertion of the nail in the bone, and a second configuration wherein the element is projecting from an opening slot of said sleeve;
wherein:
a proximal pair of said shape memory elements is provided at the rod proximal end and a distal pair of said elements is provided at the rod distal end;
the shape memory elements of the proximal pair lie on a same plane and are kept in their corresponding seats by a proximal cover;
the shape memory elements of the distal pair lie on a offset plane with respect to the plane of the elements of the proximal pair, and are kept in their corresponding seats by a distal cover; and the distal cover is formed by two portions that are connected by one corner and are extended in perpendicular planes.

2. The intramedullary nail according to claim 1, wherein the first and second shape memory element of the distal pair are 90° angularly spaced one from the other.

3. The intramedullary nail according to claim 1, wherein one shape memory element of the distal pair is located on a plane at 45° with respect to the plane of the elements of the proximal pair while the other element of the distal pair is located on a plane at −45° with respect to the plane of the elements of the proximal pair.

4. The intramedullary nail according to claim 1, wherein said shape memory elements are realized by SIM (Stress Induced Martensite) materials.

5. The intramedullary nail according to claim 4, wherein said SIM material is Nitinol.

6. The intramedullary nail according to claim 1, wherein both said portions have an outside concave surface that reproduces the continuity of the cylindrical rod when the distal cover is mounted and fixed to the rod to keep in position the distal couple of shape memory elements.

7. The intramedullary nail according to claim 1, wherein said proximal cover is formed by an elongated portion integrally formed with a tubular top portion including an internal thread corresponding to the thread internally formed at the proximal end of the rod.

8. An intramedullary nail to be inserted into a fractured elongated bone comprising:
a cannulated rod extending between a proximal end and a distal end;
an outside tubular sleeve for hosting said rod, the rod being coaxial with the sleeve and axially or angularly guided inside the tubular sleeve;
shape memory elements hosted in corresponding seats of said rod; each element being able to assume a first configuration wherein it is retractably housed in its respective seat, so to allow the insertion of the nail in the bone, and a second configuration wherein the element is projecting from an opening slot of said sleeve;
wherein:
a proximal pair of said shape memory elements is provided at the rod proximal end and a distal pair of said elements is provided at the rod distal end;
the shape memory elements of the proximal pair lie on a same plane and are kept in their corresponding seats by a proximal cover;
the shape memory elements of the distal pair lie on a offset plane with respect to the plane of the elements of the proximal pair, and are kept in their corresponding seats by a distal cover; and
said proximal cover is formed by an elongated portion integrally formed with a tubular top portion including an internal thread corresponding to the thread internally formed at the proximal end of the rod.

9. The intramedullary nail according to claim 8, wherein the first and second shape memory element of the distal pair are 90° angularly spaced one from the other.

10. The intramedullary nail according to claim 8, wherein one shape memory element of the distal pair is located on a plane at 45° with respect to the plane of the elements of the proximal pair while the other element of the distal pair is located on a plane at −45° with respect to the plane of the elements of the proximal pair.

11. The intramedullary nail according to claim 8, wherein said shape memory elements are realized by SIM (Stress Induced Martensite) materials.

12. The intramedullary nail according to claim 11, wherein said SIM material is Nitinol.

* * * * *